United States Patent [19]

Flegel et al.

[11] Patent Number: 4,515,715

[45] Date of Patent: May 7, 1985

[54] L-ALANYL-D-ISOGLUTAMINE ADAMANTYLAMIDE

[75] Inventors: Martin Flegel; Milan Krojidlo; Jirí Kolínský; Karel Masek; Jaroslav Seifert, all of Prague, Czechoslovakia

[73] Assignee: SPOFA, spojene podniky pro zdratvonickou vyrobu, Prague, Czechoslovakia

[21] Appl. No.: 509,293

[22] Filed: Jun. 29, 1983

[30] Foreign Application Priority Data

Jun. 29, 1982 [CS] Czechoslovakia .................... 4908-82

[51] Int. Cl.³ .......................................... C07C 103/52
[52] U.S. Cl. ............................................ 260/112.5 R
[58] Field of Search ................. 260/112.5 E, 112.5 R; 424/177

[56] References Cited

U.S. PATENT DOCUMENTS 4,273,704 6/1981 Mazur .......................... 260/112.5 E

FOREIGN PATENT DOCUMENTS 0098520 6/1983 European Pat. Off. ............ 424/177

Primary Examiner—Delbert R. Phillips

[57] ABSTRACT

The invention relates to L-Alanyl-D-isoglutamine adamantylamide of the formula

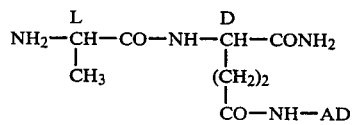

wherein AD represents a residue of adamantane bound in the number 1 position. The described compound evidences an immunostimulatory and immunoadjuvant activity of unusual degree without any relevant side effects such as pyrogenity.

1 Claim, No Drawings

L-ALANYL-D-ISOGLUTAMINE ADAMANTYLAMIDE

This invention relates to a novel dipeptide derivative and to a method for preparation thereof. More particularly, the present invention relates to L-alanyl-D-isoglutamine adamantylamide which evidences significant immunoadjuvant and immunostimulatory activity.

It is well known that there is a lack of compounds capable of enhancing the defensibility of an organism by stimulation of the immune response. At one time, bacterial products or fragments of cellular walls were used for this purpose. Unfortunately, clinical use of this approach often resulted in deleterious side effects or in non-standardized effects. This difficulty has also been encountered with compounds having immunoadjuvant activity wherein bacterial products from Mycobacterium tuberculosis are primarily employed, typically in combination with mineral oils.

However, some progress in this field has been attained by the use of active sub-units of bacterial walls, either enzymatically or synthetically (F. Ellouz et al, Biochem.Biophys.Res. Commun. 59, 131/, 1974). The bulk of experimental effort with these materials was done with muramyl dipeptide (N-acetyl-muramyl-L-alanyl-D-isoglutamine, MDP) See L. Chedid et al, Progr. Allergy 25, 63 Karger, Basel, 1978); and (C. Merser et al, Biochem.Biophys.Res. Commun. 66, 1316, 1975) and several of its analogs. In these analogs, biological effects are represented in different degrees and studies have revealed that the peptidic part of the molecule is critical for both adjuvant and immunostimulatory effects, and further that this activity is essentially independent of the carbohydrate residue of the molecule (L. Chedid et al, C. Merser et al, l.c.; K. Masek et al, Experientia 35, 1397, 1979; S. Kotani et al, Biken's J. 18, 105, 1975; A. Hasegawa et al, Agric.Biol.Chem. 42, (11), 2187, 1978).

It has also been reported that the effect of MDP and its analogs may be increased and greater stability achieved when they are administered in either a mineral oil medium or when bound to liposomal structures (J. Freud and K. McDermot, Proc.Soc.Expt.Biol.Med. 49, 548, 1942; K. Masek et al, Experientia 34, 1363, 1978). In those cases in which the synthetically prepared compounds were biologically active they were usually found to be pyrogenic, no negating their use for clinical purposes. It has also been suggested that adjuvant effects are directly connected with pyrogenity (S. Kotani et al, Biken's J. 19, 9 1976).

Other studies revealed that a predominant lipophility of the molecule plays a significant role in its biological activity. This has been verified by preparing structural analogs with a higher alkyl radical attached to the oxygen atom of the hydroxyl group in position 5 of a saccharide moiety (S. Kotani et al, Biken's J. 18, 105, 1975). A similar effect was also observed by introducing an aliphatic lipophilic chain into the isoglutamine molecule (K. Masek et al, Experientia 35, 1397, 1979).

In accordance with the present invention, a novel type of immunostimulatory material is attained by introducing a residue of adamantane into the gamma-carboxamide group of the isoglutamine moiety. The resultant L-alanyl-D-isoglutamine adamantylamide, hereinafter referred to as "ADP" is of the general formula

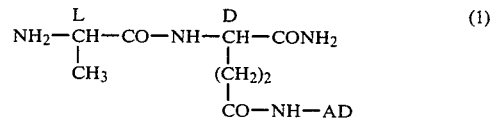

wherein AD represents a residue of adamantane bound in its number one position. The ADP described herein has been found to possess remarkable immunostimulatory activity and does not evidence pyrogenity or other undesirable side effects.

The ADP of the invention may be conveniently prepared by the use of techniques employed in the preparation of peptides, preferably by reacting a protected L-alanyl-D-isoglutamine derivative with 1-aminoadamantane. Thus, for example 1-aminoadamantane may be reacted with a dipeptide derivative of the formula

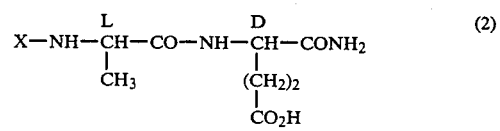

wherein X represents a protective group capable of being removed by acidic hydrolysis or by hydrogenation (hydrogenolysis) during which the protective group is split off. Suitable protective groups for this purpose include tert-butyloxycarbonyl, benzyloxycarbonyl and nitrophenylthio groups.

Specific examples of the preparation of the compound of the invention are set forth below. It will be appreciated by those skilled in the art that these examples are set forth solely for purposes of exposition and are not to be construed as limiting.

EXAMPLE 1 t-Butyloxycarbonyl-L-alanyl-D-isoglutamine 20.3 grams of dicyclohexyl carbodiimide was added to a solution of 19.6 grams of BOC-ala and 12.3 grams of N-hydroxybenztriazole in 280 ml dioxane at $-10°$ C. The mixture was stirred for 1 hour at room temperature and filtered. The filtrate was then added to a solution of 13.3 grams of D-isoglutamine in 60 ml of water and stirring continued overnight. Then, the reaction mixture was filtered and the filtrate evaporated to dryness. The evaporation residue was then recrystallized from ethylacetate ether. The product yield was 30.9 grams (83% of theoretical), m.p. 98° C., $(\alpha)_D^{20} - 8.2$ (c 1, methanol).

EXAMPLE 2 t-Butyloxycarbonyl-L-alanyl-D-isoglutamine adamantylamide 1.9 grams of 1-aminoadamantane hydrochloride base was treated with a 2N sodium hydroxide solution and the released base extracted with chloroform. 1.4 grams (9 mmoles) of the base obtained by evaporation was dissolved in 30 ml of dimethyl formamide and the solution cooled to $-10°$ C. This solution was then mixed with a solution of 2.1 grams (10 mmoles) of dicyclohexyl carbodiimide in 10 ml of dimethylformamide. After 5 minutes, a solution of 1.6 grams (5 mmoles) of BOC-ala-D-iGln, 1.3 grams of N-hydroxybenztriazole, 0.7 ml of triethylamine and 5 ml. of pyridine in 20 ml of dimethylformamide was added. The mixture so obtained was then stirred at room temperature overnight. Following, dimethylformamide was evaporated and 100 ml of ethyl acetate added, the solution then being repeatedly extracted with 0.1N hydrochloric acid and a 5% sodium hydrogen carbonate solution, dried and evaporated. Precipitation of a methanolic solution of the evaporation residue with water yielded 1.28 grams (56% theoretical) of the desired compound. Elementary and amino acid analysis corresponded with theoretical.

EXAMPLE 3

L-Alanyl-D-isoglutamine adamantylamide

A t-butyloxycarbonyl group was split off from the product of Example 2 by treating the product with a 40% solution of trifluoroacetic acid in methylene chloride. After standing for 1 hour at room temperature, the solution was evaporated and the residue mixed with ether. 0.9 grams of the product (in the form of a trifluoroacetate) was obtained by suction and dissolved immediately in 5 ml of ethanol. Then, the product in solution was brought on the column of an anion exchanger in OH-cycle and eluted with methanol. 0.8 grams (83% theoretical) of a foamy product was obtained by evaporation of the eluate.

Analysis of amino acid composition: Ala 1.01, iGln 0.97.

Product purity was further verified by high pressure liquid chromatography (HPLC) and by paper-electrophoresis in buffers having pH values of 2.5 and 5.7.

L.Alanyl-D-isoglutamine adamantylamide was analyzed as follows: a stationary phase (standard $C_{18}$ reverse phase sorbent) was formed by treated silica gel with lipophilic groups (column 15×0.3 cm), and a mobile phase containing 60–80%, by volume of organic modifier, preferably methanol, and from 40–20%, by volume of 0.2% aqueous trifluoroacetic acid. Detection using an ultraviolet detection was done at 210 nm. The rate of flow of the mobile phase was 20–30 ml per hour.

The purity of the product was further verified using thin layer chromatography on a thin layer of silica gel in a n-butanol-acetic acid-water (4:1:1) and chloroform-methanol-acetic acid-water (40:20:10:5) system.

0.3 grams of a pure compound (approximately 95% by weight as deduced from the peak area) was obtained by HPLC purification of 0.5 grams of crude product, and used for pharmacological tests.

The pharmacological properties of L-alanyl-D-isoglutamine adamantylamide were determined as follows:

TEST NO. 1

The immunoadjuvant effect was tested in guinea pigs by application into their left back paw of a 0.2 ml mixture of ovalbumin (2.5 mg) and 100 μg of L-alanyl-D-isoglutamine adamantylamide (ADP) in incomplete Freunds adjuvant (FIA). For comparative purposes, incomplete Freunds adjuvant with ovalbumin was administered. The effects of the compound being tested were then compared with a known strongly active bacterial adjuvant, Mycobacterium tuberculosis. To this group of animals, there was administered a mixture containing ovalbumin with complete Freunds adjuvant (FCA). The effect of the compound of the invention was also compared with the effects of N-acetylmuramyl-L-alanyl-D-isoglutamine (MDP). Three weeks after the administration of the test materials, the skin reaction of guinea pigs was determined after the administration of 10 and 20 μg of ovalbumin. The results of the skin reaction tests are set forth in Table 1, below.

TABLE 1

| Induction of delayed hypersensitivity to ovalbumin in guinea pigs with synthetic ADP | | | |
|---|---|---|---|
| | | Dermatic response after 24 hours (mm) | |
| Tested substances | Dose | Ovalbumin dose 10 μg | Ovalbumin dose 20 μg |
| FIA | — | 1.0 ± 0.48 | 3.39 ± 0.22 |
| FCA | 1 mg | 3.71 ± 0.23+/ | 5.73 ± 0.33+/ |
| MDP | 100 μg | 2.99 ± 0.23+/ | 6.07 ± 0.21+/ |
| ADP | 100 μg | 2.70 ± 0.21+/ | 5.82 ± 0.27+/ |

The numbers represent the average values of two experiments in 16 animals.
+/statistically significant differences / p ≦ 0.05/
Explanatory notes:
FIA = Freunds incomplete adjuvant (Bayol + Arlacel 4:1)
FCA = Freunds complete adjuvant (Bayol + Arlacel: 1 mg of mycobacterium tuberculosis)
MDP = N—acetyl-muramyl-L-alanyl-D-isoglutamine
ADP = L-alanyl-D-isoglutamine adamantylamide It will be noted by reference to Table 1 that the administration of the described compound resulted in the enhancement of delayed hypersensitivity in guinea pigs to ovalbumin and that a dosage of 100 μg was comparable to the effect of both MDP and FCA.

TEST NO. 2

Labelled thymidine is frequently used for the study of biosynthesis of DNA in vivo. This preferred pyridine desoxynucleoside is phosphorylated to dTTP (desoxy-thymidinetriphosphate) in a succession of phosphorylation reactions. dTTP is the immediate precursor of DNA synthesis in the cell nucleus. The enhancement of labelled thymidine incorporation into DNA represents activation of its biosynthesis which precedes cell propagation.

This test is perhaps one of the most logical and reliable tests for determining immuno-stimulating effects of substances and their effect on cell propagation.

MDP in a dose of 1.00 mg/kg and ADP in a dose of 0.74 mg/kg were administered in equimolar concentrations to Wister male rats weighing 150 to 160 grams. The animals were killed after 16 hours. Two hours prior to being killed, thymidine (methyl-$^3$H) was administered to them intraperitoneally in a dose of 20 μCi per animal in a 0.3 ml physiological solution (specific activity 20 Ci: (mmole).

Frozen organs were then taken out of the animals and promptly homogenized in 0.2N $HClO_4$. After repeated washing of the sediment with 0.2N $HClO_4$, RNA was removed by alkaline hydrolysis. Then, nucleotide components were released from protein-DNA precipitate by hydrolysis in 1N $HClO_4$. Following neutralization, the supernatent was evaporated to dryness. Nucleotides of DNA were next transferred to bases by further acidic hydrolysis in concentrated $HClO_4$. Thymine was then isolated in chromatographically pure form by repeated paper chromatography and radioactivity determined using a scintillation spectrometer. The results of this test are set forth in Table 2, below.

TABLE 2

| Utilization of (methyl - $^3$H) thymidine for synthesis of DNA of liver, kidneys, thymus and spleen of rats after MDP and ADP administration | | | | |
|---|---|---|---|---|
| | cpm/uml DNA of thymine | | | |
| | liver | kidneys | thymus | spleen |
| Controls | 1.750 | 1.750 | 940 | 11.150 |
| MDP (muramyl-dipeptide) | 4.100 | 2.350 | 1.400 | 10.900 |

TABLE 2-continued

Utilization of (methyl - ³H) thymidine for synthesis of DNA of liver, kidneys, thymus and spleen of rats after MDP and ADP administration

| | cpm/uml DNA of thymine | | | |
|---|---|---|---|---|
| | liver | kidneys | thymus | spleen |
| ADP (adamantyl-dipeptide) | 2.950 | 2.200 | 1.550 | 16.500 |

The data set forth in Table 2 reveal that a single administration of ADP in a dose of 0.75 mg/kg has a pronounced positive effect on the incorporation of methyl-³H thymidine into the thymus and spleen DNA. These two organs participate to a substantial extent in the development of tumor and cell immunity. Furthermore, the tabular data manifest a significant enhancement of thymidine utilization for the synthesis of thymus DNA which is of the same order of magnitude as in the case of MDP, the effect of which has long been known. With respect to the spleen, the administration of MDP is not accompanied by enhanced thymidine utilization; however, ADP has a pronounced stimulating effect manifested by enhanced ³H thymidine utilization.

The results presented with respect to the effect of MDP in the utilization of thymidine for the synthesis of spleen DNA are in agreement with the data shown in the literature, such data revealing that MDP has no effect on this organ, even on isolated spleen cells in vitro. Comparison of the invention reveals that the compound of the invention is superior due to the fact that it exerts the desired action on both organs and playing an important role in the immune reaction.

TEST NO. 3

The synthetic MDP analogs of the prior art generally evidence immunoadjuvant and immunostimulative effects in addition to pyrogenic properties which represents a significant limitation in clinical practice. This fact has prevented several very promising substances from being used clinically. In this experiment, the pyrogenic effect of ADP was compared with the effect of MDP. ADP was intravenously administered to rabbits of 1.8 to 2.0 kg by weight in a dose of 100 μg/kg and the effects compared with those of the same dose of MDP. The same volume of isotonic solution (6.2 ml) was then injected into control animals in which the basal temperature was measured for 6 hours with a rectal thermistor thermometer in 1 hour intervals. The results are set forth in Table 3, below.

TABLE 3

Pyrogenic effects of MDP and ADP in rabbits

| Tested substance | Dose | Temperature, °C. | | | | | |
|---|---|---|---|---|---|---|---|
| | | 1 hour | 2 hours | 3 hours | 4 hours | 5 hours | 6 hours |
| Controls (only isotonic solution) | — | −0.1 | +0.2 | −0.2 | −0.1 | 0 | +0.1 |
| ADP | 100 μg/kg | +0.3 | +0.4 | +0.4 | +0.4 | +0.3 | +0.35 |
| MDP | 100 μg/kg | +0.8 | +1.7 | +1.8 | +1.3 | +0.7 | +0.4 |

The values presented in Table 3 are the average values of 5 animals in a group.

Analysis of Table 3 reveals that ADP has no pyrogenic effect in doses contemplated for clinical application. However, in the same dose of 100 μg/kg MDP is clearly pyrogenic. The fact that ADP is free of any pyrogenic effect with retained immunostimulatory and immunoadjuvant effects is of considerable advantage and suggests real possibilities for clinical application.

The results of the pharmacological evaluation of the described compound reveal that in the form of an immunostimulatory pharmaceutical preparation in a mixture with conventional pharmaceutical auxiliary substances may be used for stimulating the immune response of organisms especially for enhancing their resistance in the state of diminished antibody formation.

Although preferred examples of the invention have been described, it will be understood that modifications may be made within the spirit and scope of the appended claims. It will also be understood that there is no intension to include unmentioned ingredients other than minor impurities.

We claim:

1. L-Ananyl-D-isoglutamine adamantylamide of the formula

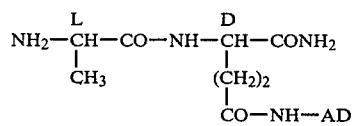

wherein AD represents a residue of adamantane bound in the number 1 position.